United States Patent [19]
Misra et al.

[11] Patent Number: 5,422,831
[45] Date of Patent: Jun. 6, 1995

[54] ACOUSTIC AND VIDEO IMAGING SYSTEM FOR QUALITY DETERMINATION OF PHARMACEUTICAL PRODUCTS

[75] Inventors: Manjit K. Misra; Yuh-Yuan Shyy, both of Ames, Iowa

[73] Assignee: Iowa State University Research Foundation, Inc., Ames, Iowa

[21] Appl. No.: 196,844

[22] Filed: Feb. 15, 1994

Related U.S. Application Data

[63] Continuation-in-part of Ser. No. 924,195, Aug. 3, 1992, Pat. No. 5,309,374.

[51] Int. Cl.⁶ .............................................. G06F 19/00
[52] U.S. Cl. .................................. 364/552; 356/407; 382/128
[58] Field of Search .................. 356/407; 364/552; 382/1, 8

[56] References Cited

U.S. PATENT DOCUMENTS

2,661,090 12/1953 Garrett ................................. 209/107
5,309,374 5/1994 Misra et al. ......................... 364/552

Primary Examiner—Edward R. Cosimano
Attorney, Agent, or Firm—Flehr, Hohbach, Test, Albritton & Herbert; Kevin J. Zimmer

[57] ABSTRACT

A flexible system for determining the quality of pharmaceutical products based on characteristics such as, for example, mass, shape, hardness, size, color and surface texture is disclosed herein. The quality determination apparatus includes a feeder assembly for sequentially dropping individual product samples upon an impact transducer arrangement. The impact transducer generates transducer signals indicative of the physical characteristics of each product sample. In addition, an imaging device operates to synthesize a digital image representation of each product sample. The transducer signal and digital image representation corresponding to each product are analyzed so as to determine the appropriate degree of quality to be associated therewith.

22 Claims, 12 Drawing Sheets

ACOUSTIC AND VIDEO IMAGING SYSTEM FOR QUALITY DETERMINATION OF PHARMACEUTICAL PRODUCTS

The United States government has certain rights in the invention pursuant to contract No. ITA 87-02 between the U.S. Department of Commerce and Iowa State University.

This is a continuation in part of copending application Ser. No. 07/924,195, filed Aug. 3, 1992, now U.S. Pat. No. 5,309,374.

The present invention relates generally to quality control of pharmaceutical products, and particularly to quality control techniques involving acoustical and video signal processing.

BACKGROUND OF THE INVENTION

Quality control of pharmaceutical products, e.g., tablets and pills, has become a subject of considerable interest as mass production techniques have become increasingly prevalent within the pharmaceutical industry. Methods of testing pharmaceutical products have involved determination of various quality parameters including, for example, weight, thickness and hardness. Conventional approaches to measuring these parameters have generally involved mechanical and electromechanical testing apparatus. For example, the weight measurement has been accomplished by using load cell technology, and thickness is generally measured by using electromechanical sensing. In determining hardness an increasing force is applied until the pill or tablet is ruptured. A hardness value is then calculated in accordance with an empirical relationship relating applied force to displacement of the product surface. Unfortunately, however, this technique for hardness determination results in destruction of the product under test.

In the agricultural industry efforts have been made to use computer-assisted imaging, rather than mechanical techniques, to facilitate recognition of defective agricultural products. Computer imaging systems generally include a color video camera connected to a frame grabber. The frame grabber digitizes the image provided by the camera and relays the image information to a computer. Analysis of the digital image information may then be performed using a variety of techniques. In particular, the potential has been shown to discriminate between crop seeds and certain common contaminants based on image parameters such as area, perimeter, aspect ratio, shape factor, and the like. Other applications have involved classification of diploid and tetraploid ryegrass seeds, and orientation determination of vegetables using grey-level intensity gradients and syntactic pattern recognition techniques.

By way of example, a computer vision system for determining soybean quality based on size and shape parameters has been developed (see Misra, et al., *Computer Vision for Soybeans*, presented at the 1989 International Summer Meeting of American Society of Agricultural Engineers and Canadian Society of Agricultural Engineering, Paper No. 89-3001). Images of a soybean are first captured using a charge-coupled device (CCD) camera and digitized by a frame grabber. The image processing sequence is initiated by determining an outline of the soybean under analysis by searching for contrasts between the portions of the image corresponding to the background and to the soybean itself. A routine is then used to fit an ellipse to the outline, since acceptably healthy soybeans were found to be generally elliptical in shape. While capable of successfully discriminating between soybeans having varying degrees of quality, it is believed that the efficiency of the machine vision system described above could be improved by modification of particular aspects of the disclosed image processing sequence.

Concurrent with the development of the image processing techniques described above, efforts have been made to develop acoustical methods of analysis based on the transmittance, absorption or reflection of sound waves by agricultural products. These techniques are based on the realization that even minor changes in the structure or health of a product will result in variation of its acoustic properties. Such variations can be quantitatively evaluated by analyzing the frequency components of the sound wave. Frequency data is generally processed using analytic procedures such as the Fast Fourier Transform (FFT), which can be performed to identify the ways in which selected frequencies are absorbed, transmitted or reflected by the product being investigated. These frequency response characteristics can be correlated with various physical properties of the product related to quality.

In the particular case of the analysis of soybeans, at least two types of acoustical methods have been investigated (see, e.g., Misra, et al., *Acoustic Properties of Soybeans*, Transactions of the American Society of Agricultural Engineers, 33(2):671–677). In a first, or "acoustic transmission" technique, a soybean kernel is placed between transmitting and receiving transducers where the former introduces an acoustic impulse to the kernel and the latter records the wave transmitted through the kernel. Both waves, the input and the transmitted, can be digitally recorded and analyzed by a Fast Fourier Transform. The two spectra can then be compared, usually by dividing the transmitted wave by the input wave to identify frequencies that are preferentially absorbed by the kernel so as to provide an indication of kernel quality. Specifically, quality may be determined by analyzing the differences in the absorption spectra of a "good" or reference soybean and the soybean under scrutiny. Unfortunately, the acoustic transmission spectra of an ideal soybean has been found to be difficult to describe mathematically. Accordingly, correlation between the transmission spectra and size or mass of the soybean has not been possible, thus precluding effective quality determination. Moreover, the placement of each soybean between the transducers has been found to be a relatively slow process.

A second, or "impact-force" method of acoustical characterization of soybeans involves dropping soybeans through a guide tube coupled to a piezoelectric force transducer. An impact signal generated by the transducer is routed to a digitizer and then to a computer. A computer program then operates to derive the frequency spectra of the impact signal by using an FFT algorithm. As in the acoustic transmission technique, correlation of the frequency spectra of the impact signal with a set of quality parameters requires the spectra to be mathematically described. Such a description could be effectuated through, for example, polynomial approximations, sine functions, or simple Bessel functions. Although the impact-force method has been shown to allow for faster determination of soybean quality, the frequency-domain procedure outlined above is relatively computationally intensive. That is, the procedure requires an initial FFT conversion of the impact signal into the frequency domain and a subsequent parameterization of the spectral characteristics so obtained. It is thus believed that a time-domain method for analyzing the transducer signal produced by an impact-force apparatus would allow for a more rapid determination of the quality of articles such as agricultural products, pharmaceutical products, and other similarly shaped edible material (e.g., hard candy).

While image processing and acoustical techniques have each been of separate assistance in determining quality within the agricultural field, it is believed that a novel system incorporating both of these methodologies would allow for increased testing flexibility in agricultural and other industrial applications. For example, when employed within the pharmaceutical industry such an integrated system would allow a user to specify that a set of product characteristics derived from both the acoustical and video realms constitute the basis for acceptable quality.

OBJECTS OF THE INVENTION

It is an object of the present invention to provide a system for determining the quality of pharmaceutical products in which is incorporated both image processing and acoustical techniques.

SUMMARY OF THE INVENTION

The present invention addresses the need for a flexible system for determining the quality of pharmaceutical products based on characteristics such as, for example, mass, hardness, shape, color and surface texture. The inventive quality determination apparatus includes a feeder assembly for sequentially dropping individual product samples upon an impact transducer arrangement. The impact transducer generates transducer signals indicative of particular physical characteristics of each product sample. In addition, an imaging device operates to synthesize a digital image representation of each product sample. The transducer signal and digital image representation corresponding to each product are then analyzed so as to determine the appropriate degree of quality to be associated therewith.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENT

Figure 1A:
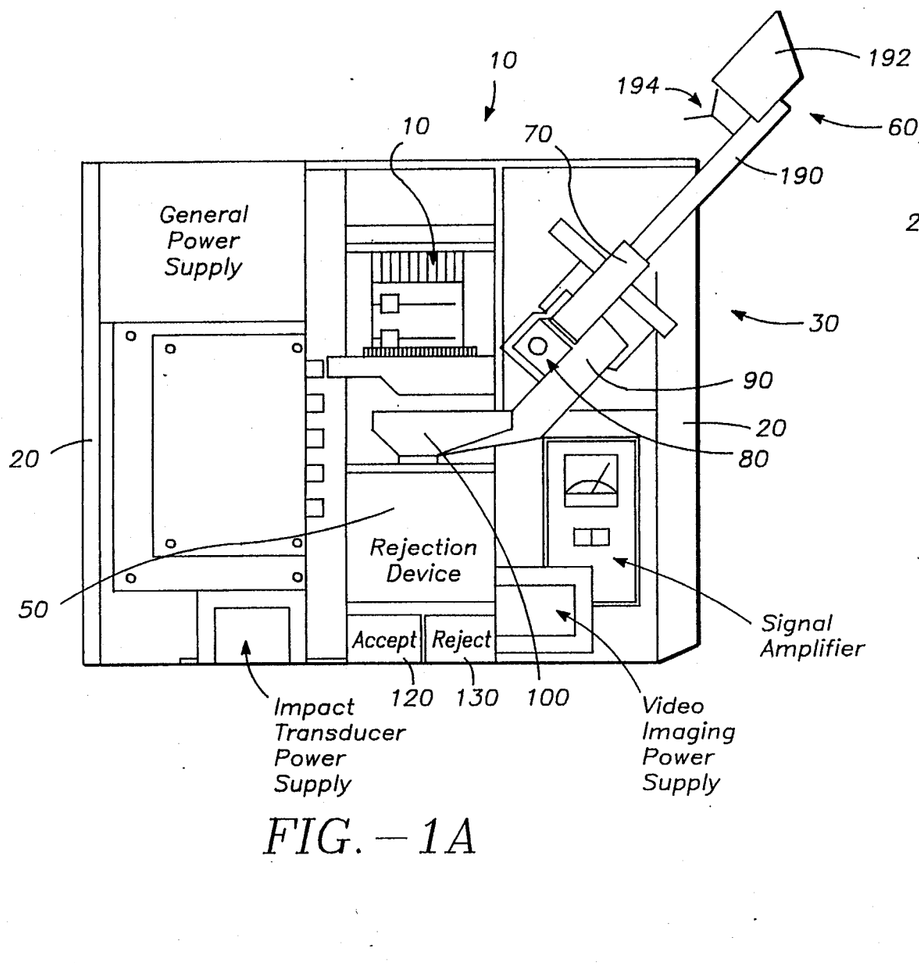
FIGS. 1a and 1b show a see-through side view and a front view, respectively, of a preferred embodiment of the pharmaceutical product quality determination system of the present invention.
Figure 1B:
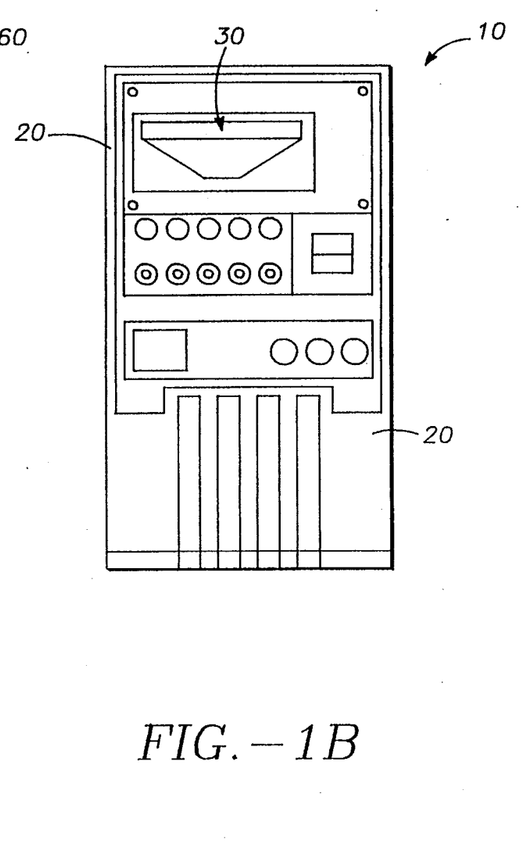

Description of Mechanical Apparatus:

Referring to FIGS. 1a and 1b, there are shown a see-through side view and a front view, respectively, of a preferred embodiment of the pharmaceutical product quality determination system 10 of the present invention. The inventive system 10 is adapted to analyze relatively firm pharmaceutical products, such as pills, tablets and capsules. Nonetheless, it is understood that the specific mechanical implementation of the system 10 depicted in FIG. 1 may be modified to accommodate analysis of pharmaceutical products of varying size and firmness. It is further understood that although the following detailed description makes specific reference to pharmaceutical pills as being the subject of analysis, the teachings of the present invention are equally applicable to pharmaceutical tablets, capsules and the like.

The quality determination system 10 is enclosed within a housing 20 and includes a drop tube feeder apparatus 30, a video imaging device 40, and a quality control rejection device 50. As is described in detail below, the pills or other pharmaceutical products to be analyzed are loaded into a roller-feed device 60 included within the feeder apparatus 30. The device 60 feeds one pill at a time to a drop tube 70. Each pill then slides down tube 70 and falls upon an impact transducer 80. An acoustical impact signal generated by the transducer 80 is then digitized and routed to a computer (not shown) for analysis. Based on this analysis the quality of the pill may be evaluated in terms of mass and hardness. The pill is deflected by the transducer 80 into a U-channel trough 90, which guides the pill to a holding bin 100.

The video imaging subsystem 40 operates to create a digital image representation of the pill while it is confined in the holding bin 100. The digital image representation of the pill is then processed so as to enable a determination of quality to be made on the basis of parameters such as lustre, color, shape and roughness. The inventive system 10 is designed such that a user may specify the extent to which each of the acoustical and image parameters mentioned above contributes to the criteria used in making an overall assessment of pharmaceutical product quality. As shown in FIG. 1A, the rejection device 50 routes pills to either accepted pill bin 120 or rejected pill bin 130 from the holding chamber 100 in accordance with such a composite quality evaluation.

Figure 2:
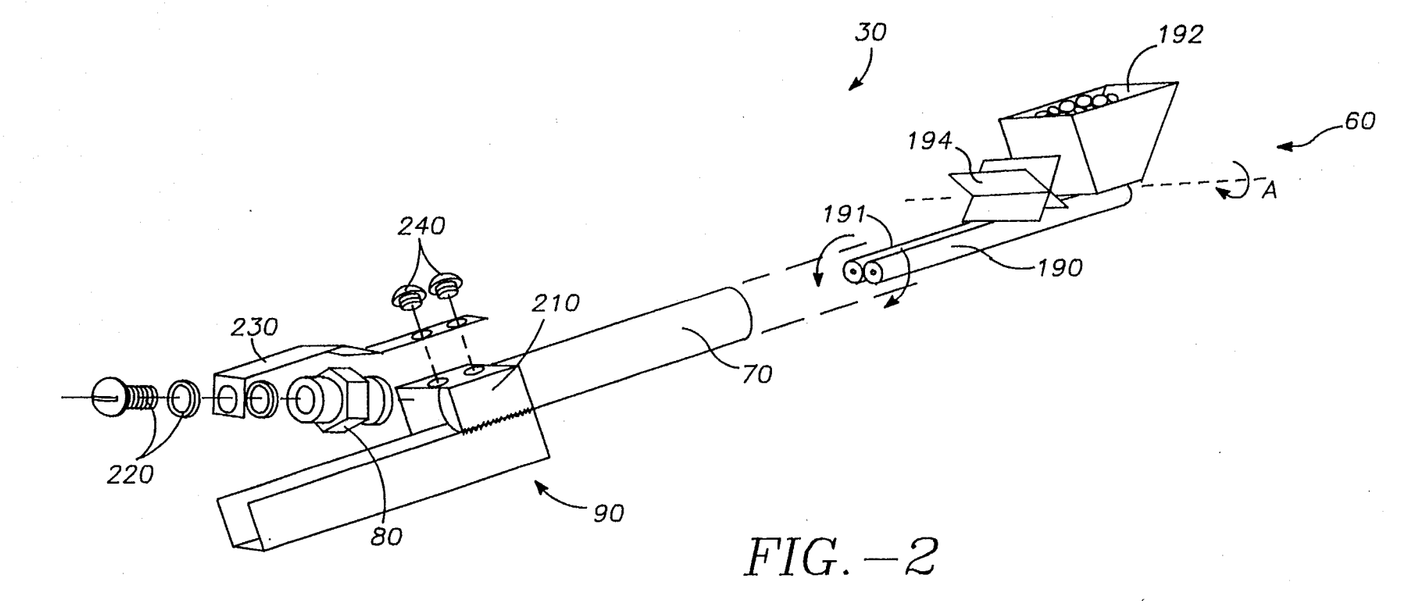
FIG. 2 provides a detailed view of a partially disassembled drop tube feeder apparatus.

FIG. 2 depicts the drop tube feeder apparatus 30 in a partially disassembled configuration. The roller-feed device 60 is of a type in which a pair of rollers 190 and 191 turn in opposite directions so as to convey each pill to be analyzed to the tube 70. Such a device is described in, for example, U.S. Pat. No. 2,661,090, entitled SORTING MACHINE, issued Dec. 1, 1953, which is herein incorporated by reference. It is understood other apparatus for providing individual pills to the tube 70 may be utilized without departing from the scope of the present invention. Referring to FIG. 2, the pills to be analyzed are loaded into a hopper 192. From the hopper 192 the pills pass through an aperture (not shown) to a rubberized 3-blade star wheel 194 disposed to rotate about an axis A. The star wheel 194 revolves at a rate about the axis A selected to ensure that the delay between pills dropped into the tube 70 is sufficient to allow for adequate signal processing of the data accumulated for each pill. The spacing between the rollers 190 and 19 1 is adjusted based on the expected size of the pills to be received from the star wheel 194. In the preferred embodiment the rollers each rotate at a rate of approximately 3,000 r.p.m.

Again referring to FIG. 2, the drop tube 70 is typically approximately 4 inches in length, is oriented at 45 degrees relative to vertical, and extends into a rectangular coupling member 210 of the U-channel trough 90. The impact transducer 80 is secured by hardware 220 to a third bracket 230, with the third bracket 230 being affixed to the coupling member 210 using hardware 240. The bracket 230 serves to position the impact transducer 80 such that pills falling from the drop tube 70 are deflected by the transducer 80 into the $\frac{3}{4}''$ U-channel trough 90. The transducer 80 may be implemented with, for example, a conventional impact transducer manufactured by PCB Piezotronics of Depew, N.Y., part no. 208A02. Subsequent to deflection by the transducer 80, each pill slides through the U-channel trough 90 into the holding bin 100.

Figure 3:
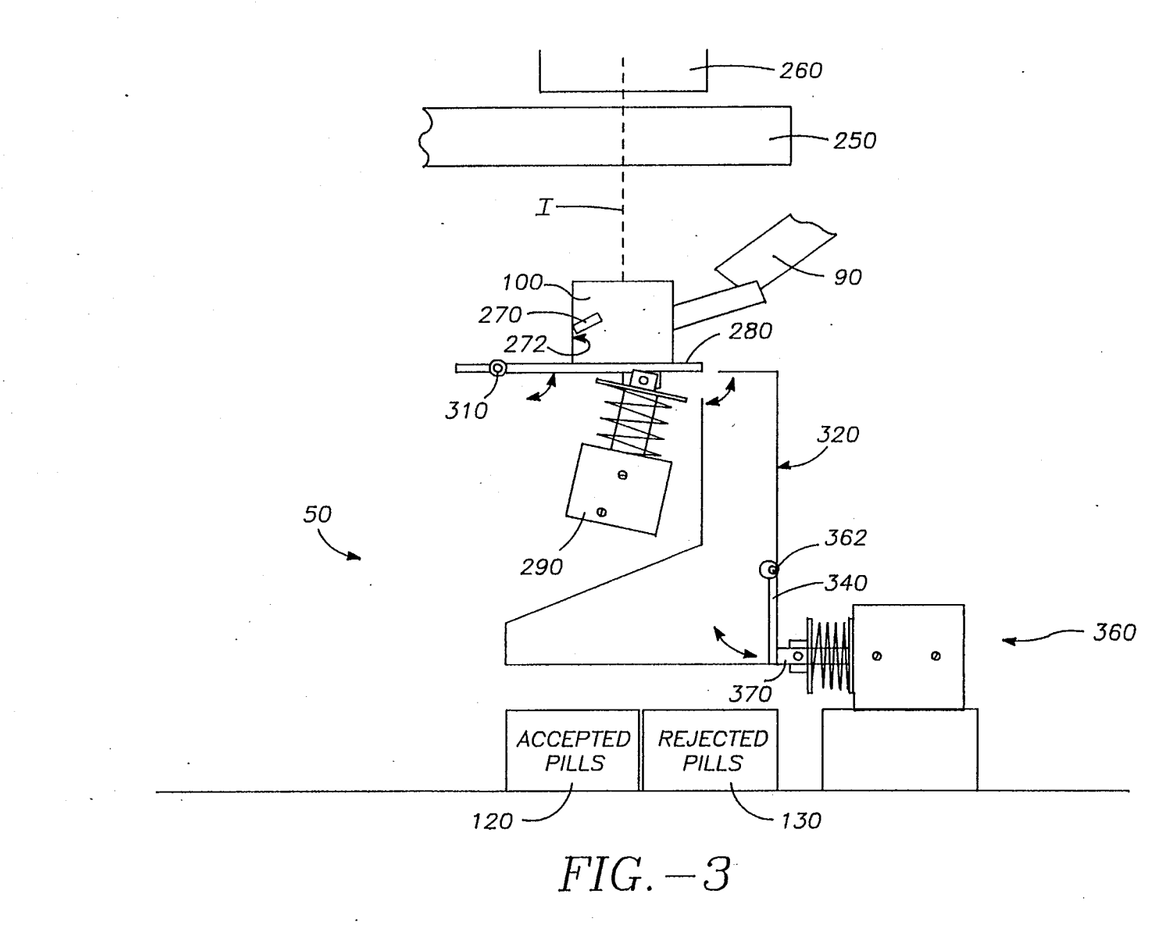
FIG. 3 shows a more detailed side view of an pharmaceutical product holding bin and product rejection device.

FIG. 3 shows a more detailed side view of the holding bin 100 and rejection device 50. Also shown in FIG. 3 is U-shaped fluorescent lighting source 250 interposed between the holding bin 100 and a lens element 260 of the video imaging device 40. The imaging device 40 is designed to create a digital image representation of each pill entering the holding bin 100 from the trough 90. Such an imaging system could be conventionally realized using an arrangement consisting of a camera, and a frame grabber. Preferably, however, the imaging device 40 will be implemented with an integrated unit similar to, for example, a conventional slide scanner. A slide scanner having suitable resolution is available from RasterOps Corp. of Santa Clara, Calif., as the "Expresso". The device produces either standard NTSC or PAL video output, and images can be captured by a computer using a frame grabber board.

Referring to FIG. 3, lens element 260 is in optical alignment with an image axis I, while the U-shaped lighting source 250 partially encircles the axis I. The lighting source 250 provides uniform illumination over the surface of pills within the holding bin 100, and may be implemented with, for example, a 110 Volt fluorescent tube. The imaging device 40 is triggered to create an image of the contents of the holding bin 100 following impact of a pill upon the transducer 80. Again, the impact signal generated by the transducer 80 may be monitored to determine the precise time at which a pill collides with the transducer 80. As is discussed more fully below, the present invention employs an object detection scheme to determine when a pill enters the field of view of lens element 260 upon entering holding bin 100 after being deflected by the impact transducer 80. The object detection process is repeated until the imaging system 40 is successful in capturing an image of the pill. Given that many varieties of pills are white or of an otherwise light color, in the presently preferred embodiment of the inventive system 10 the interior surfaces of the holding bin 100 are painted flat black in order to improve the contrast of the digital image representation.

As is shown in FIG. 3, a photocell 270 for determining pill lustre (reflectivity) is mounted on an interior surface 272 of the holding bin 100. The photocell 270 will preferably be installed within a $\frac{3}{4}''$ diameter tube oriented downward at 45 degrees relative to the bin surface 272. The photocell 270 is disposed to continuously provide an electrical signal indicative of the amount of radiant energy from the lighting source 250 reflected by the holding bin 100 and by any pills therein. Pill reflectivity is determined by sampling the photocell signal, generally at a sampling rate of less than 1 MHz, during an interval immediately following generation of the impact signal. Between one and three hundred samples will typically be averaged and the result compared with a background photocell signal (i.e., the signal produced by photocell 270 when no pills are present within the holding bin 100). The results of this comparison are indicative of pill reflectivity, and are stored in the memory of a host computer described below. The photocell 270 can be conventionally realized using, for example, a cadmium sulphide photocell, available from Radio Shack, Inc., part no. 276-116. Referring to FIG. 3, the holding bin 100 includes a hinged floor 280 coupled to a first solenoid 290. After an image of the pill within the holding bin 100 has been created by the imaging device 40, solenoid 290 is actuated and operates to rotate floor 280 clockwise about hinge 310. The pill resting on floor 280 then falls through chute 320 and either is collected by rejected pill bin 130, or is deflected by a hinged arm 340 into accepted pill bin 120. If the pill has been determined to be of acceptable quality a second solenoid 360 having a shaft 370 coupled by an "O" ring (not shown) to hinged arm 340 operates to rotate arm 340 clockwise about hinge 362. The falling pill is thereby deflected by arm 340 into accepted pill bin 120. The first and second solenoids 290 and 360 then return the floor 280 and arm 340 to their respective initial positions.

Figure 4:
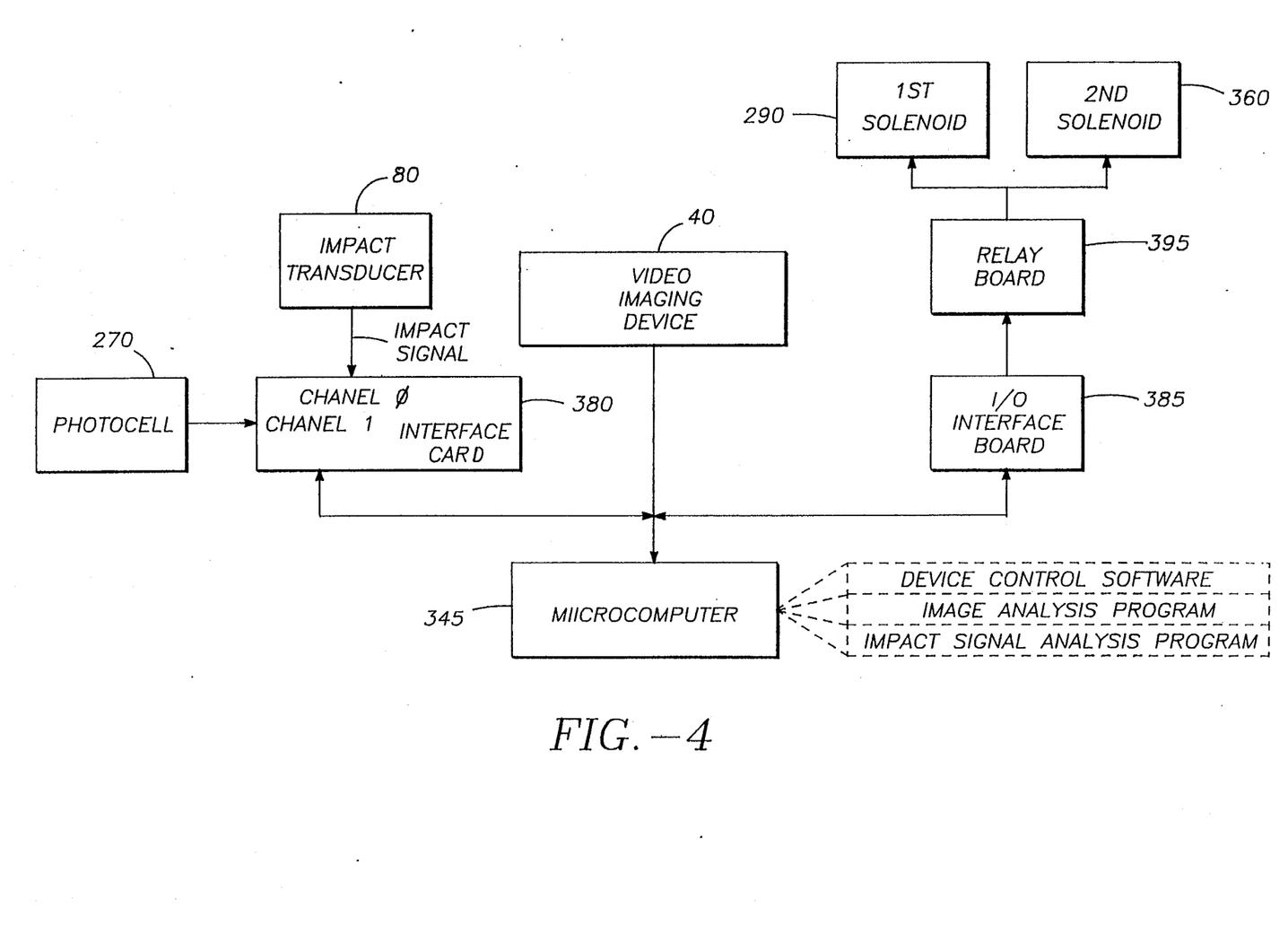
FIG. 4 provides a block-diagrammatic overview of the signal processing elements incorporated with the inventive pharmaceutical product quality determination system.

Description of Computer and Interface:

FIG. 4 provides a block-diagrammatic overview of the signal processing elements incorporated within the inventive pharmaceutical quality determination system 10. General computing capability is provided by a Gateway 386-33 microcomputer 345 operative at 33 MHz. The Gateway 386-33 includes an IBM PC/AT compatible microcomputer based on an Intel 80386-33 processor together with an Intel 80387-33 math co-processor, and also was equipped with four megabytes of random access memory (RAM), disk drives, and a hard drive. When the imaging device 40 is conventionally implemented using a standard video camera, a Targa-16 color image capture board (frame grabber) having 512 kilobytes of static RAM enables the Gateway 386-33 to digitize electronic photographs from the camera. This enables display of the digital image representation synthesized by the imaging device 40 on an analog RGB monitor or an NTSC color video monitor. The captured images exhibited 512 (horizontal) by 483 (vertical) pixel resolution, with each pixel representing one of 32,768 displayable colors.

Referring to FIG. 4, a Keithly DAS-50-1M, A/D high speed interface card 380 for digitizing the impact and photocell signals is incorporated within the microcomputer. The Keithly DAS-50 provides a 1 MHz conversion rate, and is equipped with an on-board memory buffer for locally holding data until access is requested by a transfer command from the microcomputer. The impact signal from transducer 80 is routed to channel #0 of the interface card 380, while the signal from the photocell 270 is received by channel #1. In order to access the interface card 380, a series of ASCII commands are sent by software resident within the microcomputer in accordance with the syntax for the card 380. Specifically, a procedure written in the Pascal computer language linked with an assembly language subroutine has been written to read registers of the interface card 380, and to control the transfer of information from the interface card data buffer.

Again referring to FIG. 4, the first and second solenoids 290 and 360 are controlled by the microcomputer via a PIO-12 input/output 385 board in conjunction with an ERA-01 8-channel relay board 395. A group of device functions for controlling the solenoids 290 and 360 have been written using Microsoft Macro-Assembler.

Figure 5:
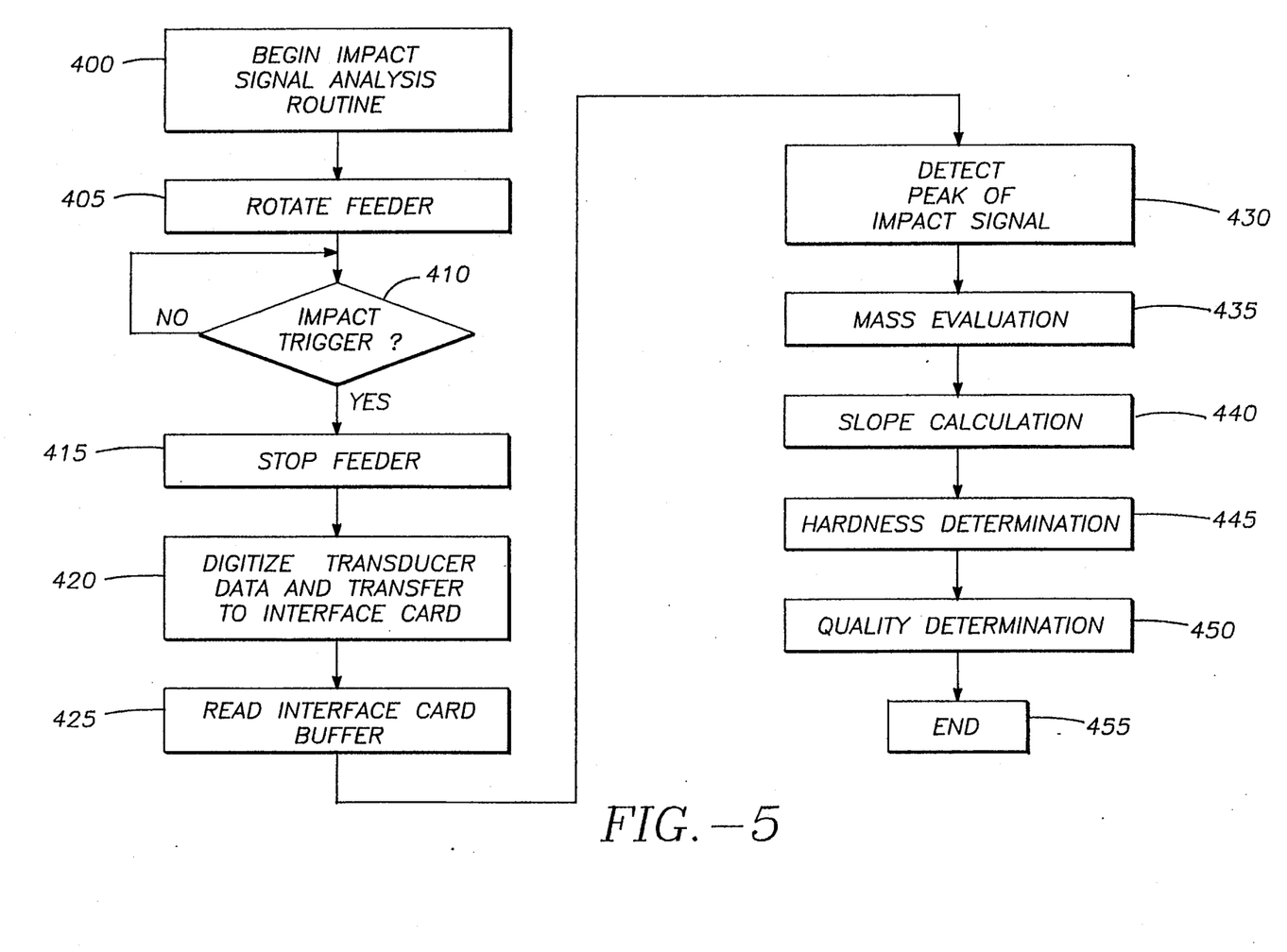
FIG. 5 shows a flow chart of a time-domain impact signal analysis routine.
Figure 6:
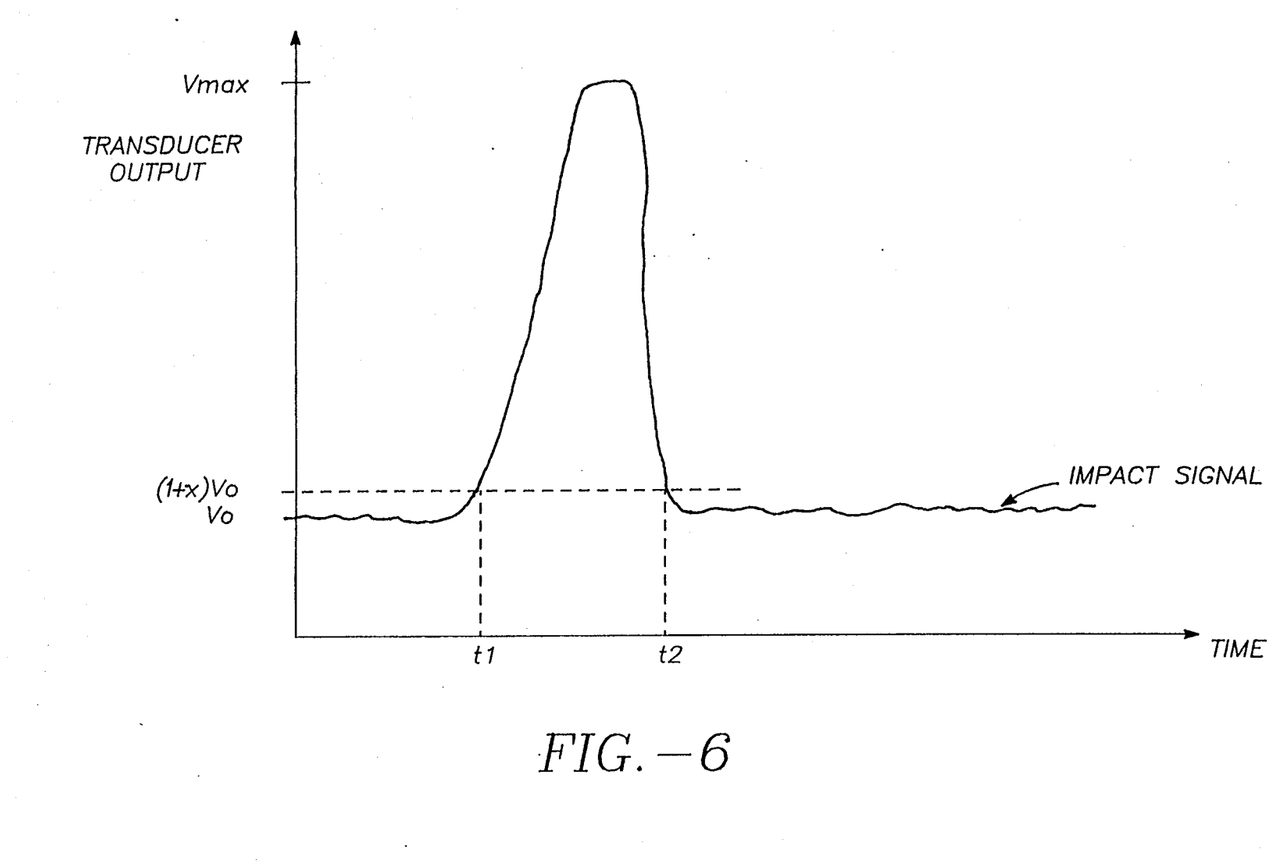
FIG. 6 illustratively represents the electrical output of the impact transducer generated in response to the impact of a sample pill thereupon.

Analysis of Impact Signal:

FIG. 5 shows a flow chart of the time-domain impact signal analysis routine. Again, the impact signal is generated in response to deflection of a pill by the impact transducer 80. The analysis routine is commenced (step 400) by rotating (405) a feeder within the drop tube apparatus 30, which results in impact of a pill upon the transducer 80. This impact is detected by monitoring (step 401) the electrical output of the transducer 80 in the manner shown in FIG. 6. As shown in FIG. 6, impact is deemed to occur (410) at time $t_1$ when the electrical output of the transducer 80 rises to a value of $(1+x)V0$, where $V0$ corresponds to the quiescent transducer output signal and the default value of x is 0.1. The feeder disk 160 is then stopped (step 415), and the impact signal is digitized by the interface card 380 (FIG. 4) at a 1 MHz sampling rate (step 420). The initial 1024 samples of the impact signal are then transferred (step 425) from the interface card 380 to the microcomputer. A largest sample value (Vmax) is then identified, and a group of ten sample values centered about the largest value (e.g., the four samples preceding Vmax and the five subsequent samples) are then avenged in order to determine a peak value proportional to pill mass (step 430). The mass of each pill may be determined by inserting (step 435) the peak value of the impact signal associated therewith into an empirical relationship stored within the microcomputer. Specifically, an empirical linear equation relating pill mass to peak impact signal magnitude may be formulated by dropping pills of known mass through the drop tube 70 and recording the magnitude of the impact signal corresponding to each.

Again referring to FIG. 6, it has been found that pill hardness is related to the spread of the impact signal proximate the peak region. This spread corresponds to the time $(t_2 - t_1)$ separating the two points at which the impact signal value is equal to $(1+x)V0$. However, since the spread of the impact signal is correlated with mass, hardness may not be uniquely determined solely on the basis of the time differential $t_2 - t_1$. Fortunately, it has also been determined that the slope of the impact signal proximate time $t_2$ is proportional to hardness and independent of pill mass. The slope at time h may be found (step 440) by approximating a straight line, hereinafter referred to as the hardness line, based on a set of values of the impact signal between Vmax and the impact signal value of $1.1V0$ at time $t_2$. A line-fitting routine such as that described by Press, et al. in *Numerical Recipes—The art of Scientific Computing*, pp. 504-505 may be used to fit this set of values of the impact signal in a minimum sum-of-squares error sense to a straight line corresponding to the hardness line (step 445).

As mentioned in the Background of the Invention, the hardness of pharmaceutical products is generally measured destructively by subjecting the product to an increasing force until rupture occurs. Accordingly, product hardness (i.e., "destructive" hardness) is often specified in terms of the force required to cause such rupture. The present invention advantageously provides a non-destructive technique for determining the hardness associated with a given pill using the hardness line. The hardness line may also be used to detect flaws in the internal structure of the pill. Specifically, it has been found that the minimum sum-of-squares error between the set of signal values used to calculate the hardness line and the hardness line itself is larger for pills that are broken, shrivelled, or of poor shape than for nondefective pills. It follows that a user-defined quality determination based on any desired combination of pill mass, hardness and internal structure may be made on the basis of the time-domain analysis of the impact signal (step 450). For example, all pills below a certain mass, or those characterized by a sum-of-squares error larger than a predefined threshold, may be classified as unacceptable. The determination of pill quality based on such a set of user-defined criteria concludes the impact signal analysis routine (step 455).

Figure 7:
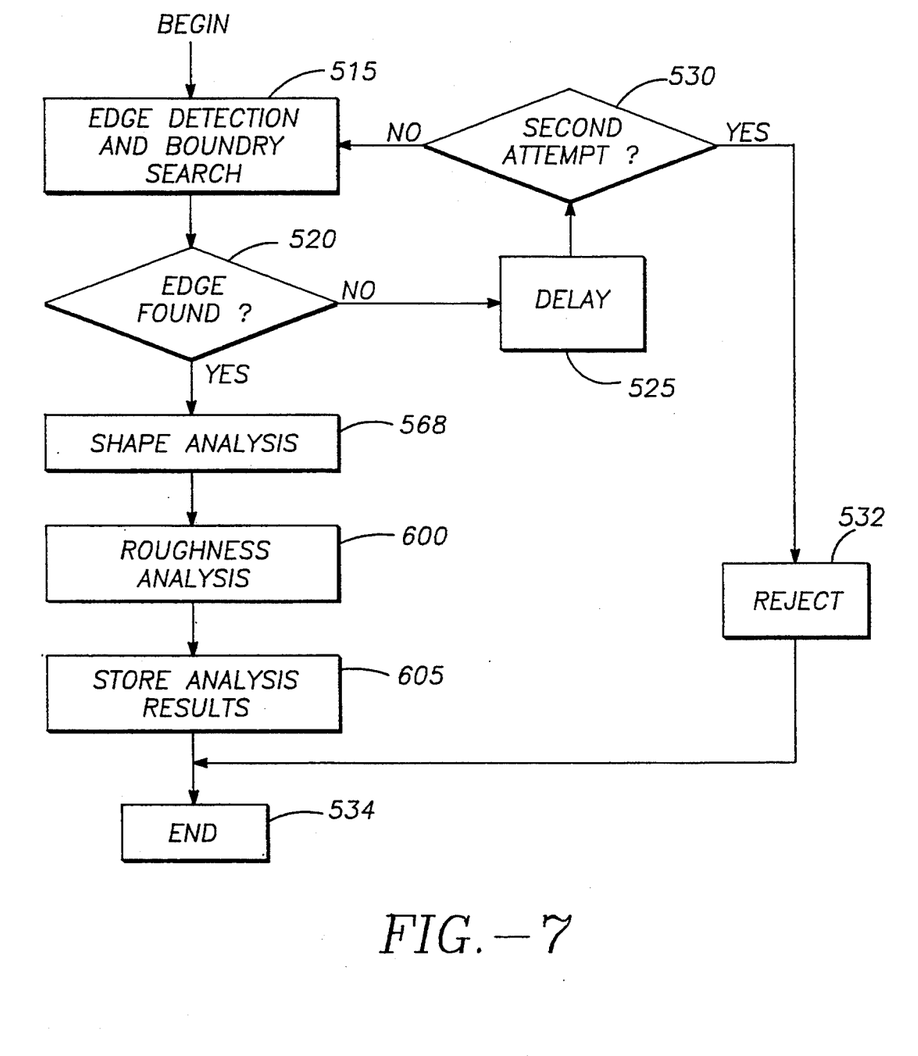
FIG. 7 depicts a flow chart of an imaging analysis routine utilized by the inventive quality determination system.
Figure 8:
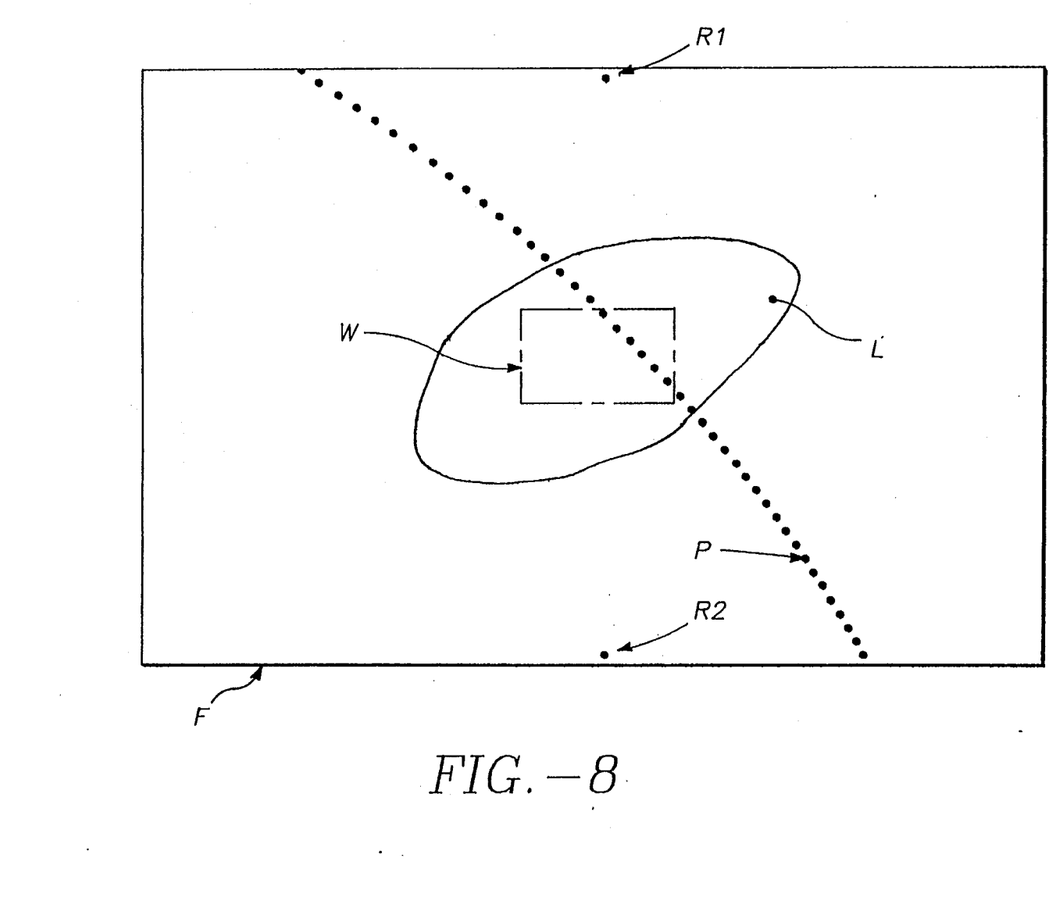
FIG. 8 depicts a simplified illustration of a digital image representation of a field of view encompassed by the imaging device included within the inventive quality determination system.

Digital Image Analysis:

Referring to FIG. 7, the first step (step 515) in the imaging analysis routine involves detecting the entrance of a pill into the field of view of the imaging device 40. Since the path taken by pills falling from the trough 90 into the holding bin 100 may be controlled by varying the angle of the trough 90, a search window within the center of the digital representation generated by the imaging device 40 may be monitored to detect the presence of pills. Specifically, FIG. 8 depicts a simplified illustration of a digital image representation of the field of view F of the imaging device 40, in which is included a pill L and upon which is superimposed a dashed line indicative of the location of a search window W and a dotted line showing the path P of pill L. A background reference is calculated for each search operation by averaging the values of first and second reference pixels R1 and R2 located proximate the periphery of the field of view F. When the average value of the approximately forty pixel elements within the search window W differs by a predetermined threshold from the background reference, a pill is deemed to exist within the window W. The microcomputer then sets a flag (step 520) to trigger the edge detection operation (FIG. 7). If a pill is not found within the search window W, the search operation is repeated until a pill is located (steps 525,530, 532 and 534). That is, the pill is rejected (532) if an edge is not detected after two or more attempts (530).

Figure 9:
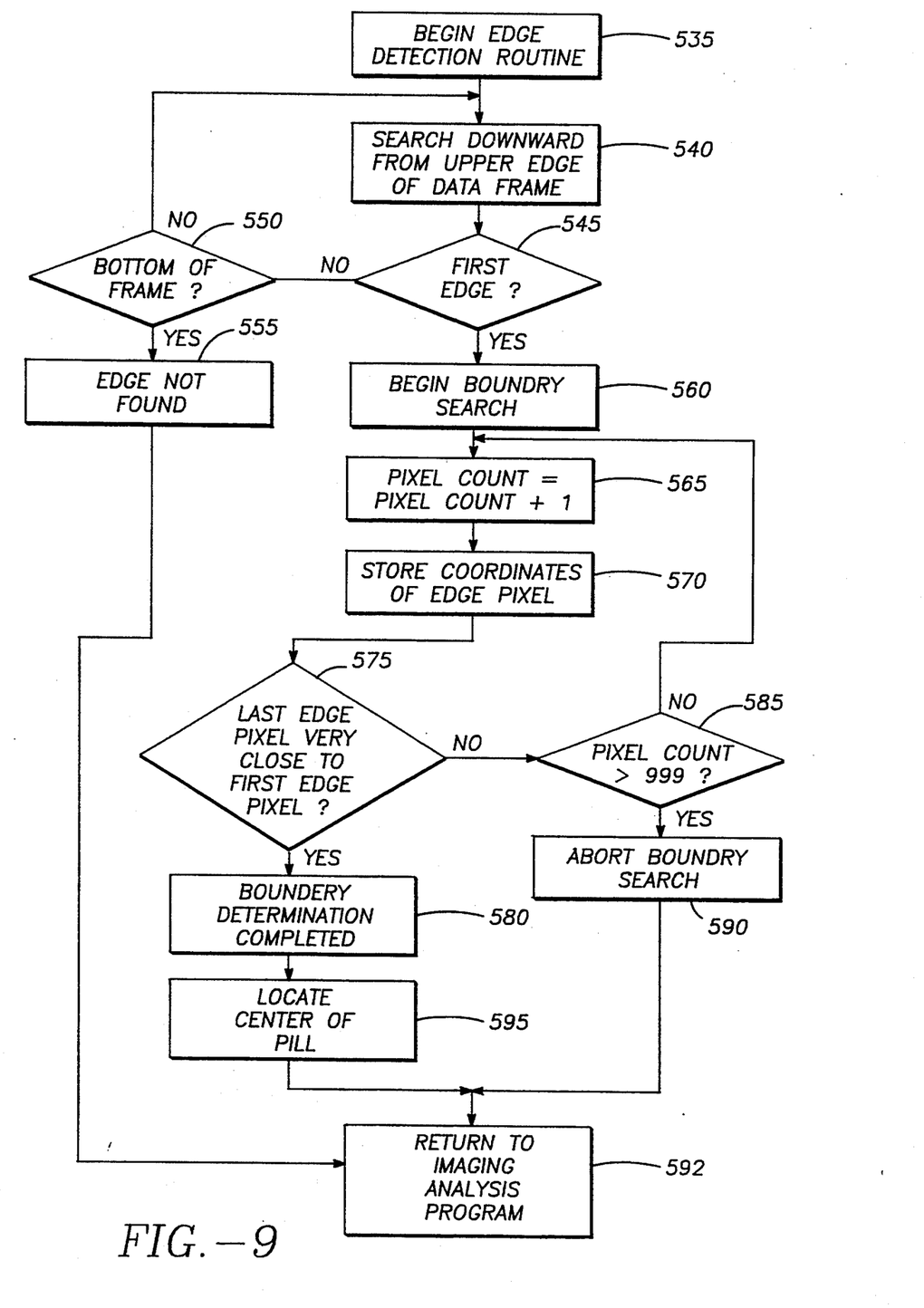
FIG. 9 is a flow chart summarizing the manner in which the edge of an image of an pharmaceutical product sample is distinguished from the background of a digital image representation thereof.

FIG. 9 is a flow chart summarizing the manner in which the edge of the pill L is distinguished from the background of the digital image representation. In particular, the pixel elements located on a vertical line originating at the upper periphery of the field of view F (FIG. 8) proximate reference pixel R1 are sequentially compared (steps 535 and 540) against the background reference. A first point on the edge of the pill L is considered to have been located (step 545) when the value of a pixel on this vertical line exceeds the background pixel value by a predetermined amount. If the lower boundary of the field of view is reached (step 550) before finding a suitably bright pixel, the program pauses and then makes a second attempt to find the pill edge.

If the pill edge is not found after a second attempt (555), control is transferred to the imaging analysis program (592).

Figure 10:
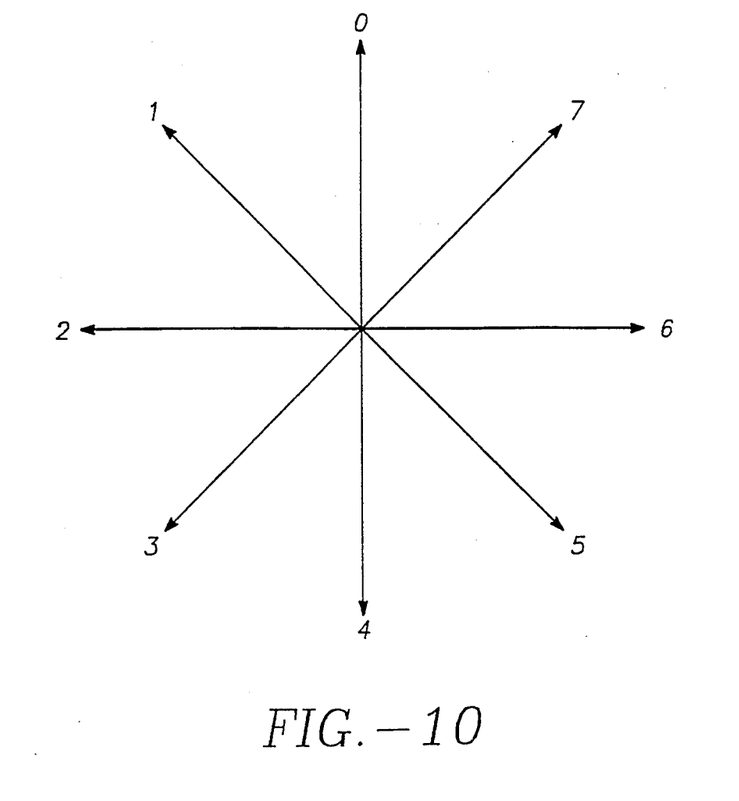
FIG. 10 illustratively represents a set of eight direction vectors used in a boundary search operation performed in connection with the digital image analysis of each product sample.

Once a first pixel point on the edge of the pill has been located, a boundary search operation is commenced (step 560). During the boundary search process a set of pixel locations located on the boundary of the pill are accumulated (step 565), thereby allowing the shape of the pill to be determined (FIG. 7, step 568). The boundary search operation proceeds in a counterclockwise manner around the edge of the pill, and involves finding the most likely direction of the next boundary pixel relative to the position of the boundary pixel last located. Specifically, FIG. 10 illustratively represents a set of eight direction vectors used in the boundary search operation. Since the search proceeds counterclockwise, after the first edge pixel has been found the value of a test pixel located left (i.e., in direction 2) of the first edge pixel by a search radius is compared with a reference value equal to the value of the first pixel less a predefined number of intensity units. If the value of the test pixel exceeds the background value it is deemed to be the second edge pixel. If the value of the test pixel is not sufficiently large relative to the reference, a second test pixel is identified by finding the pixel located in direction 3 relative to the first pixel, and separated therefrom by a distance approximately equivalent to the search radius. This process is repeated for test pixels at direction vectors 4, 5, 6, ..., etc. until a suitably bright test pixel is found. The search process may be expedited by altering the direction vector initially searched after accumulation of each edge pixel. For example, if the most recent edge pixel found is located in direction 4 relative to the previous edge pixel, direction 3 will first be searched in attempting to locate the next edge pixel. In this way the search process "remembers" the relative location of the previous edge pixel and thus more efficiently tracks the pill perimeter.

The boundary search operation results in the accumulation (step 570) of a set of pixels which approximate the pill boundary. The accuracy of the approximation may be increased by reducing the search radius, but such a reduction tends to lengthen the duration of the search process since more boundary points are accumulated. The process terminates when an edge pixel is found within an area of predefined size (e.g., a 4×4 pixel area) relative to the first edge pixel (steps 575 and 580). Alternatively, the process is aborted (steps 585, 590 and 592) if greater than a maximum number, typically on the order of one-thousand, of edge pixels are accumulated without satisfying the termination criteria mentioned above.

Next, the location of the center of the pill is calculated (step 595) using the accumulated set of boundary pixels. This calculation may be performed, for example, for a round pill by finding a diameter corresponding to the line between the most widely separated pixel locations. The location of the pill center may be approximated by finding the midpoint on this line. After the pill center has been determined, control is transferred back to the imaging analysis program (592).

Figure 11:
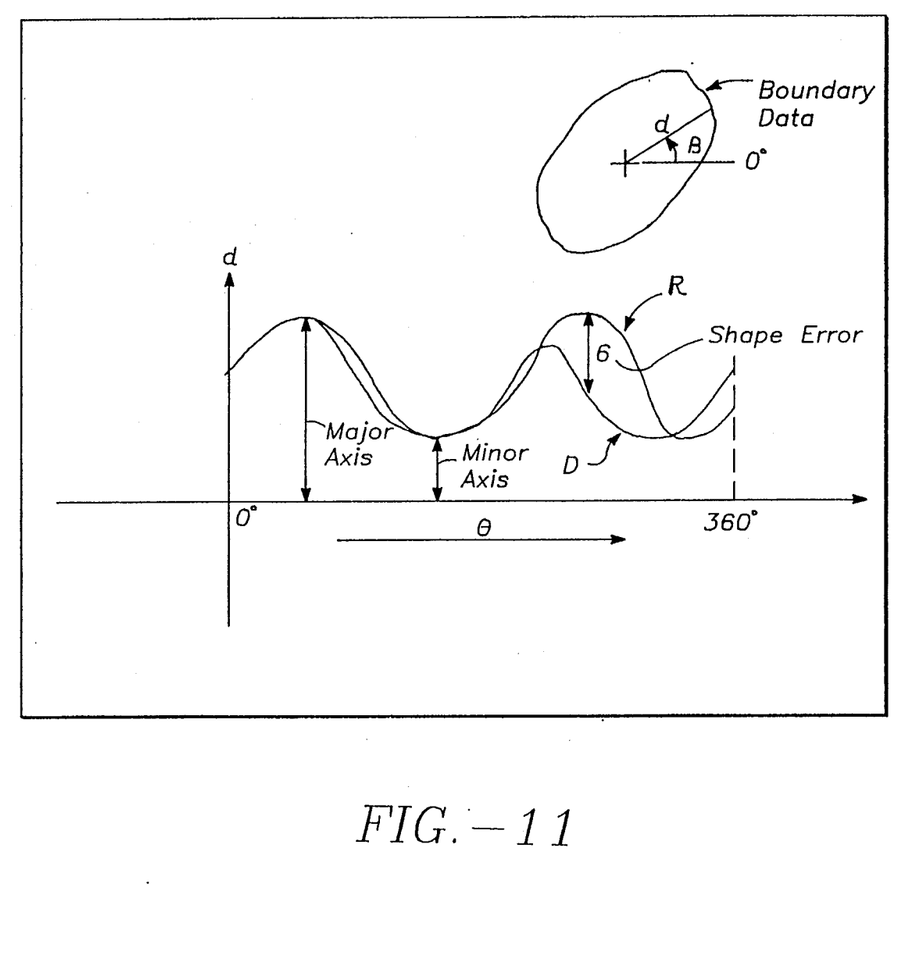
FIG. 11 depicts the manner in which the shape and the boundary roughness of each sample pill may be calculated using an accumulated set of boundary pixels and the location center of the sample pill.

FIG. 11 depicts the manner in which the shape and surface texture (roughness) of each pill may be calculated using the accumulated set of boundary pixels and the location of the center of the pill. Specifically, the boundary defined by the accumulated set of edge pixels is divided into three-hundred sixty parts ($\theta = 0$ to 359 degrees) and the distance "di", i=0 to 359, from the center to each is then calculated. The distance di may then be plotted as a function of the angle $\theta$ as shown by the edge data curve D in FIG. 11. The plot corresponding to a reference ellipse R is superimposed over the curve D by aligning the data point corresponding to the major axis of the reference ellipse with the first peak in the edge data curve D.

The roughness of the pill may be estimated (see FIG. 7, steps 600 and 605) by computing the variance between the edge data point di and its neighborhood di+1 over $\theta = 0, 1, 2, \ldots, 359$ degrees. Referring to FIG. 11, roughness may be quantified as $\Sigma(d_i - d_{i+1})^2/360$, where "i" ranges from 0 to 359. A user may indicate tolerance for roughness by specifying the maximum variance between the curves D and R to be exhibited by accepted pills. Similarly, an estimate of the extent to which the shape of the pill agrees with the reference ellipse R may be obtained by finding the error a between the reference ellipse R and the edge data curve D. Again with reference to FIG. 11, shape error may be quantified as $\Sigma\sigma_i^2/360$, where "i" ranges from 0 to 359. Again, a user may specify the maximum value of shape error to be associated with pills of acceptable quality. Finally, an indication of pill roundness may be obtained by finding the ratio of the minor axis to the major axis. The program then terminates (534) after all analysis results have been stored (605).

Figure 12:
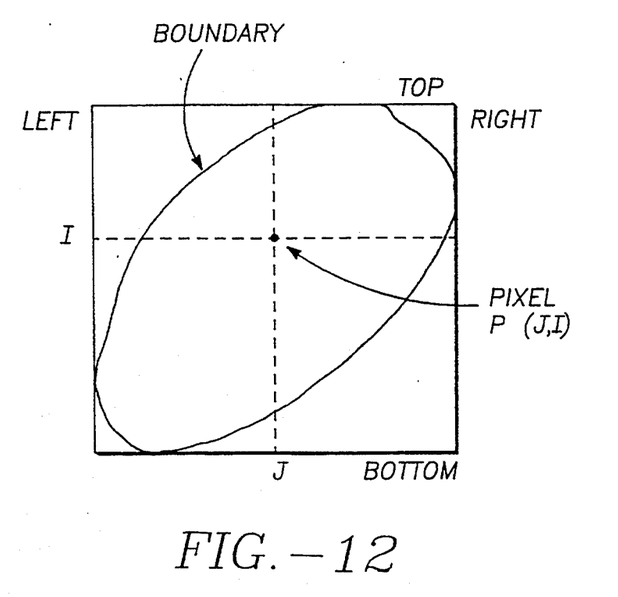
FIG. 12 depicts the manner in which the texture, area and color of the surface of each sample pill may be calculated using a pixel-by-pixel comparison and area normalization.

FIG. 12 depicts the manner in which the texture, area and color of the surface of each pill may be calculated using a pixel-by-pixel comparison and area normalization. Upon completion of the edge detection routine, a display graphics subroutine is called which superimposes a solid boundary over the set of boundary points. In addition, a calculation box is generated so as to enclose the solid boundary as indicated in FIG. 12. As is discussed below with reference to FIG. 13, a texture analysis program processes pixels from the upper left corner of the calculation box, proceeding from left to right and from top to bottom (see, e.g., steps 620, 625, 650, 655, 660, 665 and 670). The texture analysis program concludes (670) subsequent to processing of the bottom, rightmost pixel.

Figure 13:
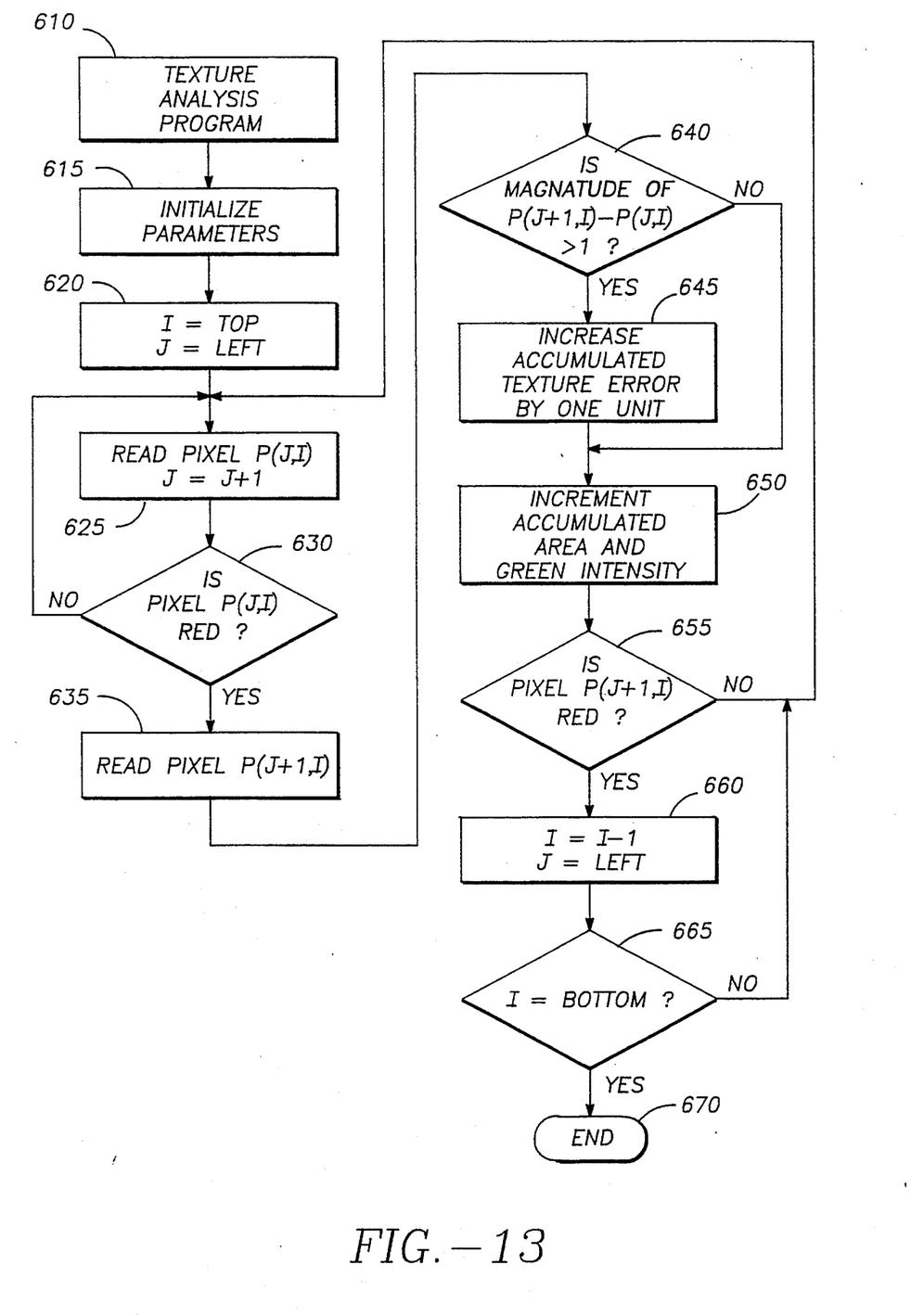
FIG. 13 is a flow chart depicting implementation of a texture analysis program.

FIG. 13 is a flow chart depicting implementation of a texture analysis and color determination program (610). Beginning in the upper left corner (steps 615 and 620) of the calculation box (FIG. 12), the difference in intensity between each pixel and its neighbor to the right is accumulated to produce an aggregate texture error. The texture error (steps 625, 630, 635, 640 and 645) is normalized by dividing the aggregate texture error by the surface area of the pill, wherein the surface area is determined by counting the number of pixels included within the pill boundary (FIG. 12). The normalized texture error relates to the prevalence of surface defects (e.g., labelling defects).

A determination of pill color may be made when the imaging system 40 is implemented with a set of three data buffers disposed to respectively store the red, green and blue intensity of each pixel element. The aggregate intensity in each buffer may then be divided by the surface area of the pill in order to obtain a normalized intensity.

In the preferred embodiment acceptable pill quality is determined by comparing the measurements associated with a given pill's shape (i.e., maximum length, minimum length and shape error), roughness, size, texture and color with a corresponding set of reference parameters. Specifically, the reference parameters Max_Length, Min_Length, Roughness, Size, Texture_Error, are determined by utilizing the image analysis program to determine average values of the aforementioned parameters for a reference set of acceptable quality (i.e., nondefective) pills. It is anticipated that the reference set will be comprised of five or more good quality pills. Deviation of the measurements associated with a pill under test more than a user-specified amount from the reference parameters indicates the test pill is, for example, broken, missing a label, or otherwise structurally defective. Table II below includes the image analysis results associated with a reference set of five acceptable quality pills. The corresponding reference parameters are specified in the row denoted as "Average". In Table III there is compiled the image analysis results for a first test batch of five broken pills. Again, the average value of each measured parameter is set forth in the row labelled average. Similarly, Table IV includes the image analysis results associated with a second test batch of five pills which are both broken and lack the identifying label imprinted on each pill within the reference set.

By comparing the average parameter values in Tables II and III, it is seen that there exists a significant deviation between Shape_Error and Roughness. Similarly, there exists significant deviation in the values of Shape_Error, Roughness and Texture_Error between Tables II and IV. In this way the image analysis routine is used to provide an indication that the pills within the first and second test batches (Tables III and IV) are of unacceptable quality.

TABLE II

| NUMBER | SHAPE ERROR | MAX LENGTH | MIN LENGTH | ROUGHNESS | SIZE | TEXTURE ERROR | COLOR IND |
|---|---|---|---|---|---|---|---|
| 1 | 0.00 | 93.80 | 85.40 | 35.10 | 152.30 | 153.76 | 122.80 |
| 2 | 0.00 | 93.80 | 85.30 | 34.50 | 152.10 | 150.36 | 122.13 |
| 3 | 0.00 | 93.80 | 85.20 | 32.80 | 152.00 | 151.32 | 123.28 |
| 4 | 0.00 | 93.80 | 85.50 | 35.80 | 151.80 | 157.68 | 122.32 |
| 5 | 0.00 | 93.80 | 85.40 | 33.80 | 151.90 | 149.86 | 123.01 |
| Average | 0.00 | 93.80 | 85.40 | 34.45 | 152.10 | 151.81 | 122.91 |
| Std | 0.00 | 0.00 | 0.00 | 0.92 | 0.28 | 2.76 | 0.15 |

TABLE III

| NUMBER | SHAPE ERROR | MAX LENGTH | MIN LENGTH | ROUGHNESS | SIZE | TEXTURE ERROR | COLOR IND |
|---|---|---|---|---|---|---|---|
| 1 | 73.60 | 94.80 | 74.80 | 258.40 | 147.80 | 175.30 | 120.88 |
| 2 | 71.00 | 94.70 | 74.80 | 254.40 | 147.90 | 171.40 | 120.13 |
| 3 | 70.10 | 94.60 | 74.80 | 271.60 | 148.20 | 178.44 | 120.91 |
| 4 | 75.00 | 94.40 | 74.60 | 256.80 | 148.80 | 173.96 | 120.74 |
| 5 | 76.00 | 94.80 | 74.50 | 256.90 | 148.90 | 171.10 | 122.02 |
| Average | 74.80 | 94.80 | 74.65 | 257.65 | 148.35 | 173.20 | 121.45 |
| Std | 1.70 | 0.00 | 0.21 | 1.06 | 0.78 | 2.97 | 0.81 |

TABLE IV

| NUMBER | SHAPE ERROR | MAX LENGTH | MIN LENGTH | ROUGHNESS | SIZE | TEXTURE ERROR | COLOR IND |
|---|---|---|---|---|---|---|---|
| 1 | 92.70 | 94.20 | 73.60 | 182.20 | 145.50 | 93.68 | 118.16 |
| 2 | 93.20 | 93.80 | 73.50 | 157.10 | 148.50 | 94.59 | 119.17 |
| 3 | 85.10 | 94.40 | 74.30 | 156.30 | 146.60 | 94.97 | 118.00 |
| 4 | 79.40 | 93.00 | 74.10 | 144.80 | 146.60 | 92.92 | 122.18 |
| 5 | 75.40 | 92.40 | 74.70 | 128.30 | 149.50 | 92.78 | 121.70 |
| Average | 84.05 | 93.30 | 74.15 | 155.25 | 147.50 | 93.23 | 119.93 |
| Std | 12.23 | 1.27 | 0.78 | 38.11 | 2.83 | 0.64 | 2.50 |

Referring to FIG. 3, pills are routed by rejection device 50 into the accepted and rejected bins 120 and 130 on the basis of the quality determinations made in regard to the impact signal and imaging analysis routines. If either analysis routine indicates that a pill is of unacceptable quality, the pill is deposited in rejected pill bin 130. It is emphasized, however, that a user may specify the extent to which each measured physical parameter contributes to the overall quality assessment made by each analysis routine.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims. For example, the teachings of the present invention may also be applied to various other edible products such as vitamin pills and tablets, candies and the like.

What is claimed is:

1. An apparatus for determining quality of a pharmaceutical product of a predefined type, comprising:

impact transducer means for generating a transducer signal indicative of a set of physical characteristics representative of composition of said product;

imaging means for synthesizing a digital image representation of physical appearance of said product; and signal processing means for analyzing said transducer signal and said digital image representation in accordance with a transducer impact signal routine and an image analysis routine respectively;

whereby, based on results of said transducer impact signal and image analysis routines, a degree of quality is associated with said pharmaceutical product.

2. The apparatus of claim 1 wherein said predefined type is included within the set consisting of pharmaceutical pills, pharmaceutical tablets, and pharmaceutical capsules.

3. The apparatus of claim 1 wherein said acoustical transducer means further includes a drop tube feeder apparatus for dropping said pharmaceutical product upon said transducer.

4. The apparatus of claim 3 wherein said imaging means includes camera means for providing an image of said pharmaceutical product and for digitizing said image so as to create said digital image representation.

5. The apparatus of claim 1 wherein said physical characteristics include mass and hardness.

6. The apparatus of claim 5 wherein said digital image representation includes information pertaining to shape and boundary roughness of said pharmaceutical product.

7. The apparatus of claim 6 wherein said signal processing means includes means for determining said shape of said pharmaceutical product based on said digital image representation, said shape determining means including means for identifying a portion of said digital image representation as corresponding to an edge of said pharmaceutical product and means for determining a center of said product relative to said edge.

8. The apparatus of claim 7 wherein said signal processing means includes means for determining roughness of said pharmaceutical product by plotting separation between predefined sections of said edge and said center and comparing said plot with a reference plot.

9. The apparatus of claim 5 wherein said acoustical transducer means includes an impact transducer, said transducer signal being generated in response to impact of said pharmaceutical product upon said transducer.

10. The apparatus of claim 9 wherein said signal processing means includes means for performing a time-domain analysis of said transducer signal.

11. The apparatus of claim 10 wherein said time-domain analysis means includes means for detecting a peak region of said transducer signal, wherein magnitude of said transducer signal at said peak region corresponds to said mass of said pharmaceutical product.

12. The apparatus of claim 11 wherein a slope of said peak signal at a predefined magnitude thereof corresponds to said hardness of said pharmaceutical product.

13. A method for determining quality of a pharmaceutical product of a predefined type comprising the steps of:

dropping said product upon an impact transducer, said transducer being disposed to generate a transducer signal indicative of a set of physical characteristics representative of composition of said product;

creating an image of said product;

digitizing said image and creating a digital image representation of said product;

storing said digital image representation in computer memory;

analyzing said transducer signal and digital image representation in accordance with a transducer impact signal routine and an image analysis routine respectively;

whereby, based on results of said transducer impact signal and image analysis routines, a degree of quality is associated with said pharmaceutical product.

14. The method of claim 13 wherein said digital image representation includes information pertaining to at least one characteristic included within the set of product characteristics consisting of surface texture, area and color.

15. The method of claim 13 wherein said step of analyzing includes the step of determining said shape of said pharmaceutical product based on said digital image representation, said shape determining step including the steps of:

identifying a portion of said digital image representation as corresponding to an edge of said pharmaceutical product, and determining a center of said product relative to said edge.

16. The method of claim 15 wherein said step of analyzing includes the step of determining boundary roughness of said pharmaceutical product by plotting separation between predefined sections of said edge and said center and comparing said plot with a reference plot.

17. The method of claim 16 wherein said predefined type is included within the set consisting of pharmaceutical pills, pharmaceutical tablets and pharmaceutical capsules.

18. The method of claim 13 wherein said physical characteristics include mass and hardness.

19. The method of claim 18 wherein said digital image representation includes information pertaining to shape and boundary roughness of said pharmaceutical product.

20. The method of claim 19 wherein said step of analyzing includes the step of performing a time-domain analysis upon said transducer signal.

21. The method of claim 20 wherein said time-domain analysis step includes the step of detecting a peak region of said transducer signal, wherein magnitude of said transducer signal at said peak region corresponds to said mass of said pharmaceutical product.

22. The method of claim 21 wherein said time-domain analysis step includes the step of determining the slope of said transducer signal at a predefined magnitude thereof wherein said slope corresponds to said hardness of said pharmaceutical product.

* * * * *